United States Patent [19]

Kehrli et al.

[11] Patent Number: 5,001,608
[45] Date of Patent: Mar. 19, 1991

[54] THERAPEUTIC LAMP EMITTING POLARIZED LIGHT

[75] Inventors: Jurg Kehrli, Jona; Armando Ulrich, Muri, both of Switzerland

[73] Assignee: "Harrier" GmbH Gesellschaft fur den Vertrieb medizinischer und technischer Gerate, Munich, Fed. Rep. of Germany

[21] Appl. No.: 358,386

[22] PCT Filed: Oct. 7, 1988

[86] PCT No.: PCT/EP88/00899
§ 371 Date: Apr. 14, 1989
§ 102(e) Date: Apr. 14, 1989

[87] PCT Pub. No.: WO89/03235
PCT Pub. Date: Apr. 20, 1989

[30] Foreign Application Priority Data

Oct. 7, 1987 [DE] Fed. Rep. of Germany ....... 3733904

[51] Int. Cl.$^5$ .............................................. F21V 9/14
[52] U.S. Cl. ..................................... 362/19; 362/264; 362/294; 128/396
[58] Field of Search ...................... 362/1, 19, 109, 264, 362/294, 373, 399; 128/395, 396

[56] References Cited

U.S. PATENT DOCUMENTS 3,185,028  5/1965  Andreoli ............................ 362/294
4,546,420 10/1985  Wheeler et al. ................... 362/19 X

FOREIGN PATENT DOCUMENTS 3049     8/1984  European Pat. Off. .
148144   7/1985  European Pat. Off. .
3220218  3/1983  Fed. Rep. of Germany .
1139096  6/1957  France .

Primary Examiner—Stephen F. Husar
Attorney, Agent, or Firm—Michael N. Meller

[57] ABSTRACT

Therapeutic lamp emitting polarized light, comprising a housing of three consecutive parts which define a common interior space, the first part being a handle having a substantially tubular form, the second part being a dome-shaped middle portion attached to an end of the handle, and the third part being a cylindrical frontal portion attached to the middle portion, the frontal portion having an axis which forms a first obtuse angle with the axis of the handle. A light source assembly with closed inner space is arranged in the interior of the housing spaced from the internal walls thereof so that an air passage channel is formed around the assembly, the assembly comprising a pair of mutually attached cylindrical tubes with axes forming a second obtuse angle being close to the first obtuse angle, a light bulb with an electrical power of at most 100 W and a reflector being attached to the first tube, a polarizer placed in the path of the light emitted by the bulb, a light filter plate for filtering out ultraviolet spectral components from the emitted light attached to the second tube, a fan being arranged in the handle to suck fresh air through the channel around the whole mantle surface of the assembly, the handle comprising slots for letting the air flow out from the inner space.

9 Claims, 3 Drawing Sheets

THERAPEUTIC LAMP EMITTING POLARIZED LIGHT

The invention relates to a therapeutic lamp, emitting polarized light, which comprises a housing which has a handle built integrally with the housing, a light bulb with an electrical power of at most 100 W arranged in the housing, a reflector arranged immediately behind the bulb, a light filter plate and a fan arranged in the housing behind the reflector.

A therapeutic lamp of the above defined type is known e.g. from the published international patent application No. WO 84/03049.

The biostimulating effects of polarized light are disclosed in the German patent specification No. DE-PS 32.20.218-C2 issued to M. Fenyô et al. FIG. 5 of this patent specification shows a therapeutic lamp, in which a polarizer filter is used. This filter is effective in the visible range of wavelengths only, therefore the infrared spectral components are filtered out. The lamp is capable of providing an output light bundle of parallel rays which has a circular cross section with a diameter of about 50 mm and the power consumption of the lamp is 150 W. This lamp substantially generates heat and a fan is used for cooling. All optical elements are arranged in a row one before the other. Owing to the high operational temperature of the casing a separate supporting structure is used.

It can be said that the lamp according to the above mentioned publication No. WO 84/03049 represents a more improved design. Here a Brewster-type polarizer is used which is effective also in the infrared range of wavelengths. Owing to the utilization of the infrared spectral components of the bulb a substantial reduction of the required lamp power could be attained. The use of a Brewster-type polarizer requires that the passageway of the light beams be tilted in a predetermined angle, in which the direction of the output beams close an angle of 114° (the twice of Brewster's angle) with the main direction of the light source. This requirement substantially affects the form of such lamps. In the above referred type of the lamp a substantially cylindrical case was used which comprised a separate handle portion and an obliquely directed frontal portion. In the frontal portion specific filter elements and a glass plate were provided to prevent the surface of the polarizer from the dust present in the sucked-in air. The cooling of the case was designed in such a way that the casing remained substantially open which could not safely prevent the sensitive light reflecting or transmitting surfaces from getting dusty with time.

The use of a large and long cylindrical casing with a separate handle made the handling of the lamp difficult, since the supporting hand had to bear not only the weight of the device but also the torque which latter became more apparent when the treatment was wholly or in part downwardly directed.

The expected life-time of a metal halogen bulb is generally about 200 hours and an inappropriate cooling can even shorten this value.

The main object of the invention is to provide an improved therapeutic lamp emitting polarized light which can be used more comfortably, has an improved protection against dust and which has a more effective cooling.

Further objects of the invention lie in the extension of the expected life-time of the bulb and in the improvement of the biostimulating effects.

According to the invention a therapeutic lamp emitting polarized light has been provided which comprises a housing, a handle built integrally with the housing, a light bulb with an electrical power of at most 100 W arranged in the housing, a reflector arranged immediately behind the bulb, a polarizer placed in the path of the light emitted by the bulb, a light filter plate for filtering out ultraviolet spectral components from the emitted light and a fan arranged in the housing behind the reflector, and the improvement according to the invention lies in that the housing comprises three consecutively and directly attached parts which define a common interior space, the first part is the handle having a substantially tubular form with an axis, the second part is a dome-shaped middle portion attached at one end to an end of the handle, and the third part is a cylindrical frontal portion attached to an other end of the middle portion, the frontal portion has an axis which closes a first obtuse angle with the axis of the handle, a light source assembly with closed inner space is arranged in the interior of the housing spaced from internal walls thereof so that an air passage channel is formed around the assembly, the assembly comprises a pair of mutually attached cylindrical tubes with axes closing a second obtuse angle being close to the first obtuse angle, the bulb and the reflector are attached to the first tube, the polarizer is arranged in the assembly, the assembly comprises light diverting means to divert selected portion of the outgoing light of the bulb towards the second cylinder, the fan is arranged in the handle to suck fresh air through the channel around the whole mantle surface of the assembly, the handle comprises slots for letting flowing air out from the inner space.

In a preferable embodiment the light diverting means is a Brewster polarizer, the second obtuse angle is twice the Brewster's angle, the tubes are cut by a plane having a normal closing Brewster's angle with both of the axes, and the polarizer comprises a plurality of spaced glass plates attached to the cut plane.

It is preferable if the filter plate closes the second tube.

The cooling will be at optimum if the assembly is arranged in the middle and frontal portions of the housing so that the spacing around the assembly will be greater close to the polarizer and narrower close to the reflector.

It is preferable if the angle between the axis of the handle and of the frontal portion of the housing is between 105° and 120°.

The holding of the therapeutic lamp will be more convenient if the handle has finger receiving depressions at the outer perimeter facing opposite direction relative to the mouth opening of the frontal portion.

The outflowing air cannot disturb the user if the slots of the handle are provided at the lower end thereof.

In a preferable embodiment of the polarizer the glass plates have elliptical forms and a metal closing plate of the same form is provided which is spaced from the rearest one of the glass plates and it is abutting the cut plane of the tubes, and the closing plate is painted black at both sides.

In a preferable embodiment the bulb is a metal halogen one built together with the reflector and in operation it is under-heated at most by 5%.

The invention will now be described in connection with a preferable embodiment thereof, in which reference will be made to the accompanying drawings. In the drawing.

Figure 1:
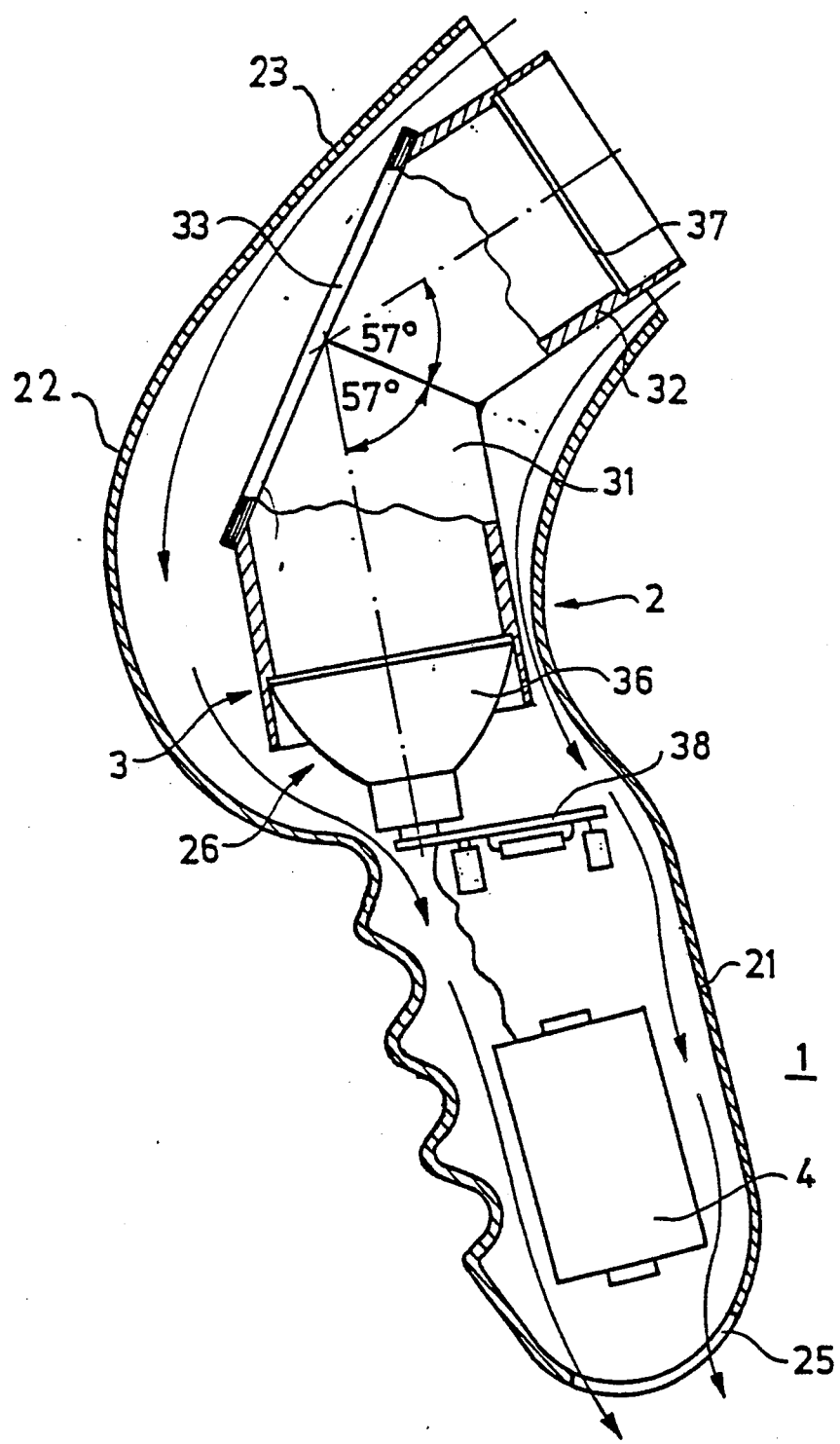
FIG. 1 shows the sectional elevation view of an embodiment of the therapeutic lamp according to the invention.
Figure 2:
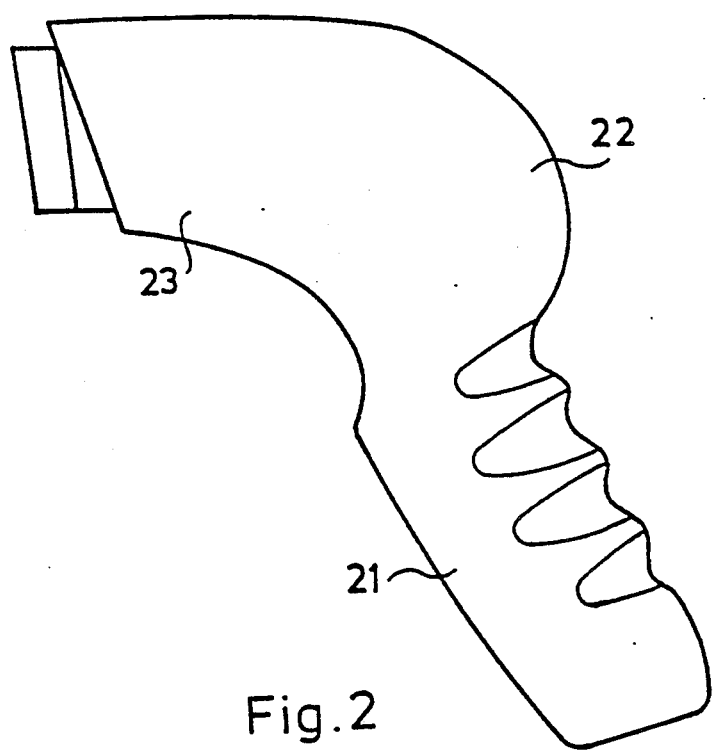
FIG. 2 shows the side view of the therapeutic lamp.
Figure 3:
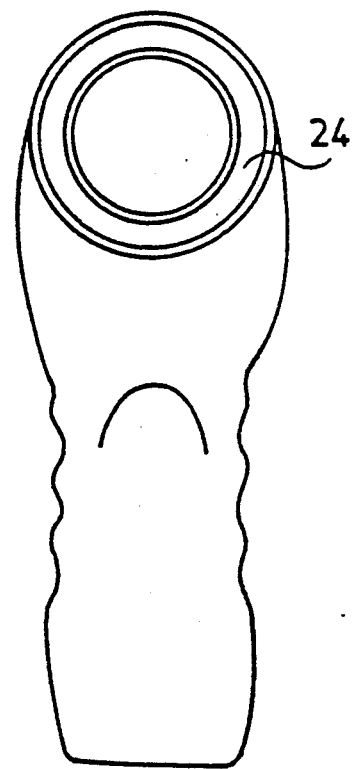
FIG. 3 shows the front view of the therapeutic lamp.
Figure 4:
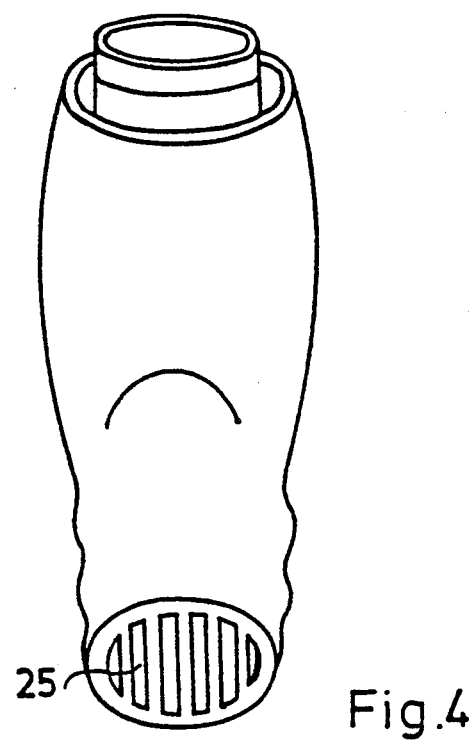
FIG. 4 shows the front view of an obliquely held therapeutic lamp.

Therapeutic lamp 1 shown in FIG. 1 comprises three main constructional parts i.e. housing 2, light source assembly 3 and fan 4. The housing 2 includes handle 21, a dome-shaped middle portion 22 and a frontal portion 23. The form of these housing parts can well be observed in FIGS. 1 to 4. The housing 2 consists preferably of a pair of conforming plastic halves which define a cavity for receiving the other constructional parts.

Light source assembly 3 is arranged concentrically in middle and frontal portions 22, 23 of the housing 2 as shown in FIG. 1, in such a way that the perimeter of the assembly 3 is always spaced from the interior wall of the housing 2. The term "concentric" intends to express that the spacing, when measured in a plane normal to that of FIG. 1, is substantially uniform. FIG. 1 shows that the light source assembly 3 is not equally spaced in the plane of the drawing.

The light source assembly 3 comprises a pair of cylindrical tubes 31, 32 made preferable from a metal like steel welded together and the axes of the tubes close an angle of 114° which corresponds to the twice of Brewster's angle. The rear part of the tubes 31, 32 is cut by a plane and the elliptic sectional surface is covered by Brewster polarizer 33. The perspective view of the light source assembly 3 can be observed in FIG. 5.

Figures 5, 6:
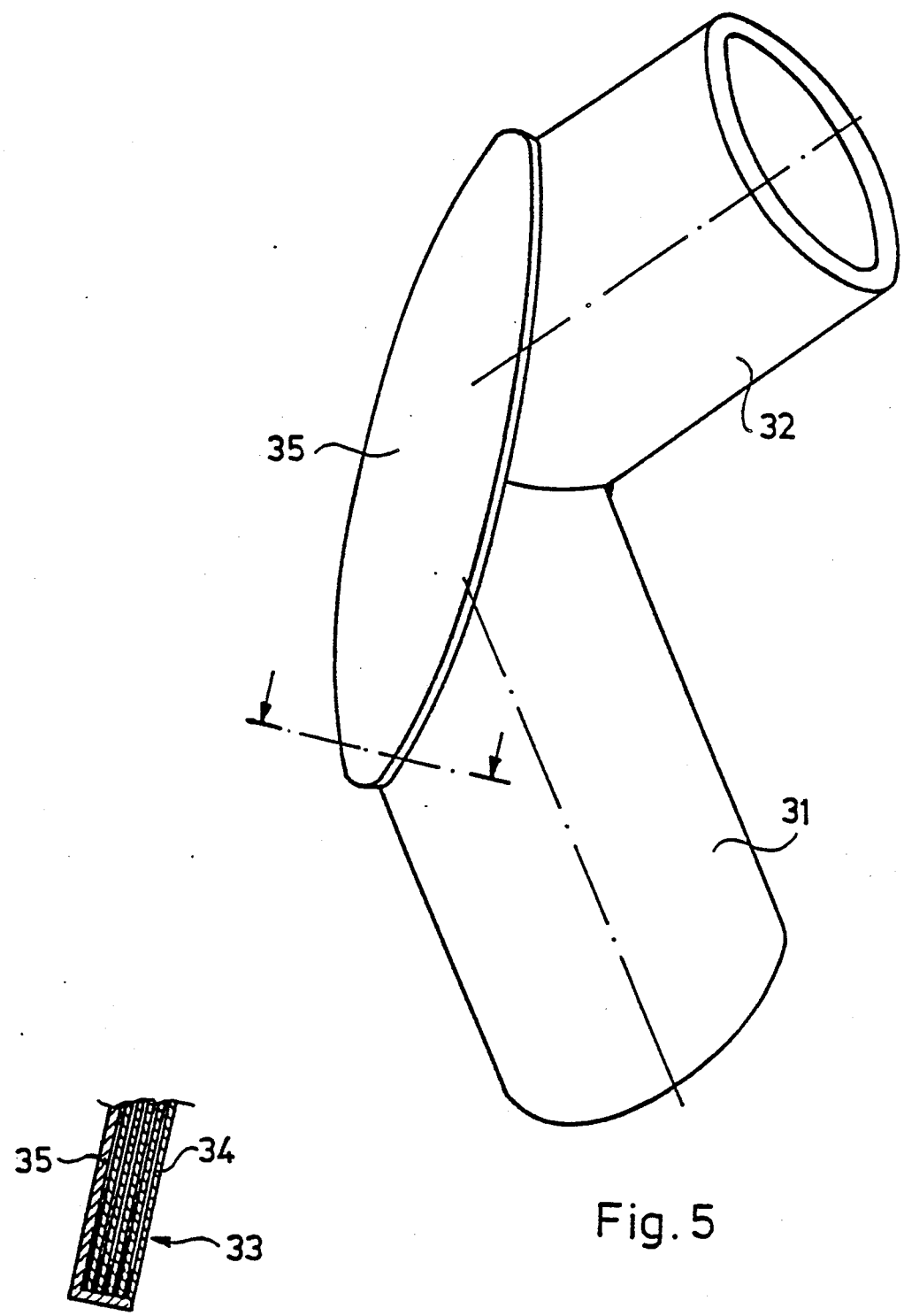
FIG. 5 shows the perspective view of the internal light source assembly.
FIG. 6 shows an enlarge detail of the Brewster-polarizer in sectional view.

FIG. 6 shows a detail of the polarizer 33 in section. The Brewster polarizer 33 comprises a plurality (e.g. five) of plano-parallel elliptical glass plates 34 which are spaced from one-another. At the rear part of the glass plates 34 an elliptical closing plate 35 is provided which is made preferably of a metal sheet and the closing plate is attached to the tubes 31, 32 so that a sealing is provided between them. For providing an improved heat transfer both surfaces of the closing plate 35 are painted black. The spacing between the glass plates 34 and between the upper plate and the closing plate 35 as well as between the lower glass plate and the elliptical supporting surface of the tubes 31, 32 is provided by thin plastic stripes.

At the rear end portion of the tube 31 a bulb 36, preferably a metal halogen bulb is provided which is built together with a reflector, and the forward rim of the reflector is pressed to a ring formed depression of the tube 31 so that a sealing is provided therebetween. The bulb 36 emits light mainly in axial direction which includes visible and infrared components and this light falls on the Brewster polarizer 33 with an angle of incidence of 57°. The power of the bulb is about 20 W but it is at any case lower than about 80–100 W, because the cooling conditions are at optimum below this limit only. The glass plates 34 of the Brewster polarizer 33 reflect the light to the direction of the axis of the second tube 32 and this reflected light is linearly polarized. The non-reflected light components fall on the black internal surface of the closing plate 35 and the generated heat is lead away by the cooling air.

The internal cavity of the light source assembly 3 is closed and sealed by yellow light filter plate 37 at the frontal end of the tube 32. The task of the light filter plate 37 is on the first hand to suppress spectral components falling below about 400–450 nm of the outgoing light of the therapeutic lamp 1 and on the other hand to seal and close the interior of the light source assembly 3, whereby the optical properties of the elements of the assembly will not be affected by any dust that would otherwise be collected thereon.

An electrical circuit board 38 is arranged near the rear end of the bulb 36 which is kept in the sketched position by means of distance members attached to the housing 2 (not shown in the drawing). The circuit board is adapted to receive internal end of a connection cord, to hold a fuse and a few number of electrical components. It can be preferable if an electrical resistance or other attenuation member is connected in series with the bulb 36 to provide an underheating of about 2 to 5%. The slight underheating of the bulb 36 increases the expected life time thereof and shifts the spectral distribution of the emitted light towards the infrared range (by decreasing the effective light-temperature), whereby the depth of penetration of the emitted light in the treated tissues will be increased. It is also possible that such a distribution is more favorable for biostimulation as well. The decrease of the light-temperature might reduce the power consumption. The underheating of the bulb 36 can also be attained by decreasing the applied supply voltage. If the nominal voltage of the bulb is e.g. 12 V, then the output voltage of a transformer feeding the bulb can be dimensioned to deliver about 11–11.4 V.

The fan 4 extends in axial direction with in the handle 21 and it sucks air through frontal inlet ring slot 24 (FIG. 3) in the space surrounding the light source assembly 3 in the housing 2. The air leaves the inner space of the housing through slots 25 (FIGS. 1 and 4) defined in the end wall of the handle 21. The cooling air flows around the whole mantle surface of the light source assembly 3, whereby a very effective cooling is accomplished. In FIG. 1 the airflow is illustrated by arrows.

The specific form of the housing 2 shown in detail in the drawings has not only aesthetically pleasing appearance but, among other things, it assists in accomplishing an effective cooling. The space around the assembly 3 has a maximum behind the closing plate 33 and at the upper end of the first tube 31 due to the doming form of the middle portion 22, and the flowing rate is sufficient to take away the heat from the large surface of the closing plate 35, and the width of the airflow channel decreases at the zone of the bulb 36, whereby the flowing rate increases significantly. In channel 26 the flow rate around the paraboloid surface of the reflector will be high and an intensive cooling takes place. This cooling ensures that the operational temperature of the bulb 36 cannot exceed the allowed upper limit. The temperature of the housing 2 will never increase more than 20° C. above the ambient temperature.

The axis of the handle 21 is slightly slanted relative to the axis of the bulb 36. From this it follows that the direction of the light rays leaving the therapeutic lamp 1 close an angle of 105°–120°, preferably 105°–110° with the axis of the handle 21. Such an angular dimensioning ensures a very pleasant support for the lamp, in which the hand grasps the handle in natural position when the rays are directed e.g. to the face of the subject.

The handle 21 comprises four radial depressions to receive four fingers of the subject. The recesses are arranged in the outward portion of the handle, while the thumb of the grasping hand can rest on the inward side of the handle. This design is optimum for self treatment which is thought to represent the most frequent use of the therapeutic lamp. The recesses are sufficiently wide and deep to provide a pleasant engagement.

In operational position the slots 25 are directed downwardly and backwardly so that the outflowing air cannot be disturbing for the subject.

In an exemplary embodiment, in which the bulb is implemented by a metal halogen bulb of 20 W power, which has a built in reflector with a mouth diameter of 50 mm, the inner diameter of the tubes 31, 32 can also be 50 mm. The therapeutic lamp emits linearly polarized light with parallel rays having a circular cross-section with a diameter of 50 mm. The light intensity measured at 20 cm from the filter plate is about 50 mW/cm$^2$.

What is claimed:

1. Therapeutic lamp emitting polarized light, comprising a housing, a handle built integrally with the housing, a light bulb with an electrical power of at most 100W arranged in the housing, a reflector arranged immediately behind the bulb, a polarizer placed in the path of the light emitted by the bulb, a light filter plate for filtering out ultraviolet spectral components from the emitted light and a fan arranged in the housing behind the reflector, wherein said housing comprises three consecutively and directly attached parts defining a common interior space, the first part being said handle having a substantially tubular form with an axis, the second part being a dome-shaped middle portion attached at one end to an end of the handle, and the third part being a cylindrical frontal portion attached to another end of said middle portion, the frontal portion having an axis which closes a first obtuse angle with the axis of said handle, a light source assembly with a closed inner space being arranged in said interior of the housing and spaced from internal walls thereof so that an air passage channel is formed around said assembly, said assembly comprising a pair of mutually attached cylindrical tubes with axes forming a second obtuse angle being close to said first obtuse angle, said bulb and said reflector being attached to a first one of said tubes, said polarizer being arranged in said assembly, said assembly comprising light diverting means to divert selected portion of the outgoing light of the bulb towards a second one of said tubes, said fan being arranged in the handle to suck in fresh air through said channel around the whole mantle surface of said assembly, said handle comprising slots for letting air flow out of said inner space.

2. The therapeutic lamp as claimed in claim 1, wherein said light diverting means comprises a Brewster polarizer, said second obtuse angle being twice the Brewster's angle, said tubes being cut by a plane having a normal closing Brewster's angle with both of said axes and said polarizer comprising a plurality of spaced glass plates attached to said tubes along said cut plane.

3. The therapeutic lamp as claimed in claim 2, wherein said filter plate (37) closes said second tube.

4. The therapeutic lamp as claimed in claim 2, wherein said assembly is arranged in said middle and frontal portions so that said spacing around the assembly is wider close to said polarizer than close to said reflector.

5. The therapeutic lamp as claimed in claim 1, wherein said first obtuse angle amounts to between 105° and 120°.

6. The therapeutic lamp as claimed in claim 1, wherein said handle has finger receiving depressions at the outer perimeter facing to an opposite direction relative to the mouth opening of said frontal portion.

7. The therapeutic lamp as claimed in claim 6, wherein said slots (25) of said handle (25) are provided at the lower end thereof.

8. The therapeutic lamp as claimed in claim 2, wherein said glass plates have elliptical forms and a metal closing plate of the same form is provided which is spaced from the rear one of said glass plates and said closing plate abutting said cut plane of said tubes, and said closing plate being black at both sides.

9. The therapeutic lamp as claimed in claim 2, wherein said bulb is a metal halogen bulb built together with said reflector and being underheated in operation at most by 5%.

* * * * *